(12) United States Patent
Vasilenko (10) Patent No.: US 11,229,716 B2
(45) Date of Patent: Jan. 25, 2022

(54) METHODS AND DEVICES FOR SANITATION, DISINFECTION AND STERILIZATION

(71) Applicant: Vitabeam Ltd, London (GB)

(72) Inventor: Vladimir Vasilenko, Martintown (CA)

(73) Assignee: Vitabeam Ltd, London (GB)

( * ) Notice: Subject to any disclaimer, the term of this patent is extended or adjusted under 35 U.S.C. 154(b) by 0 days.

(21) Appl. No.: 15/744,351

(22) PCT Filed: Jul. 14, 2016

(86) PCT No.: PCT/US2016/042183
§ 371 (c)(1),
(2) Date: Jan. 12, 2018

(87) PCT Pub. No.: WO2017/011612
PCT Pub. Date: Jan. 19, 2017

(65) Prior Publication Data
US 2018/0207302 A1    Jul. 26, 2018

Related U.S. Application Data

(60) Provisional application No. 62/192,324, filed on Jul. 14, 2015.

(51) Int. Cl.
*A61L 2/10* (2006.01)
*A61L 2/00* (2006.01)
(Continued)

(52) U.S. Cl.
CPC ............ *A61L 2/10* (2013.01); *A61L 2/0058* (2013.01); *A61L 2/0094* (2013.01); *A61L 2/084* (2013.01);
(Continued)

(58) Field of Classification Search
CPC .......... A61L 2/10; A61L 2/0094; A61L 2/238; A61L 2/24; A61L 2/202; A61L 2/085;
(Continued)

(56) References Cited

U.S. PATENT DOCUMENTS 6,030,653 A    2/2000  Rosenthal et al.
2003/0147770 A1*  8/2003  Brown .................. A61L 2/0011
                                                    422/24

(Continued)

FOREIGN PATENT DOCUMENTS

CN          2411788 Y    12/2000
CN       203400347 U     1/2014
(Continued)

OTHER PUBLICATIONS

The Chinese National Intellectual Property Administration, search report of Chinese patent application No. 2016800527695, dated Apr. 23, 2019, 4 pages.
(Continued)

*Primary Examiner* — Sean E Conley
*Assistant Examiner* — Brendan A Hensel
(74) *Attorney, Agent, or Firm* — Meunier Carlin & Curfman LLC (57) ABSTRACT

The present invention relates to methods and devices for diminishing microbes. The invention provides methods and devices to sanitize, disinfect and sterilize areas, spaces, surfaces and items as well as to sanitize human skin. The methods and devices will be of major importance to the healthcare industry and to other industries or physical environments that require sanitizing, disinfecting or sterilizing. The methods comprise the use of near infrared light (NIR), UV, violet and blue emitting LED elements as well as OLED
(Continued)

(Organic Light-Emitting Diodes) as a stand-alone technology. Optionally the system may be used in combination with ozone and ionized silver.

7 Claims, 8 Drawing Sheets (51) Int. Cl.
*A61L 2/08* (2006.01)
*A61L 2/20* (2006.01)
*A61L 2/24* (2006.01)
*A61L 2/238* (2006.01)
*A61N 5/06* (2006.01)

(52) U.S. Cl.
CPC ............... *A61L 2/085* (2013.01); *A61L 2/202* (2013.01); *A61L 2/238* (2013.01); *A61L 2/24* (2013.01); *A61N 5/0624* (2013.01); *A61L 2202/11* (2013.01); *A61L 2202/13* (2013.01); *A61L 2202/14* (2013.01); *A61L 2202/24* (2013.01); *A61L 2202/25* (2013.01); *A61L 2202/26* (2013.01); *A61N 2005/0652* (2013.01); *A61N 2005/0653* (2013.01); *A61N 2005/0659* (2013.01); *A61N 2005/0661* (2013.01); *A61N 2005/0662* (2013.01)

(58) Field of Classification Search
CPC .... A61L 2/084; A61L 2/0058; A61L 2202/26; A61L 2202/14; A61L 2202/24; A61L 2202/13; A61L 2202/11; A61L 2202/25; A61N 5/0624; A61N 2005/0662; A61N 2005/0661; A61N 2005/0659; A61N 2005/0653; A61N 2005/0652
See application file for complete search history.

(56) References Cited

U.S. PATENT DOCUMENTS

| 2008/0008620 | A1 | 1/2008 | Alkins | |
| 2009/0143842 | A1 | 6/2009 | Cumbie et al. | |
| 2011/0215261 | A1* | 9/2011 | Lyslo | A61L 2/10 250/492.1 |
| 2012/0100038 | A1 | 4/2012 | Vasilenko et al. | |
| 2012/0121457 | A1* | 5/2012 | Farren | A61L 2/10 422/3 |
| 2013/0161531 | A1 | 6/2013 | Haile et al. | |
| 2013/0175460 | A1* | 7/2013 | Farren | A61L 2/10 250/504 R |
| 2014/0060094 | A1 | 6/2014 | Shur et al. | |
| 2014/0265039 | A1 | 9/2014 | Bellec et al. | |
| 2015/0147229 | A1* | 5/2015 | Fewkes | G02B 6/0066 422/24 |
| 2015/0231288 | A1* | 8/2015 | Campagna | A61L 2/10 422/24 |
| 2015/0343235 | A1* | 12/2015 | Blanche | A61L 2/085 607/91 |

FOREIGN PATENT DOCUMENTS

| CN | 104010667 A | 8/2014 |
| KR | 20120077951 A | 7/2012 |
| WO | 2005031881 | 5/2005 |

OTHER PUBLICATIONS

European Patent Office, supplemental partial European search report of European patent application No. EP16825149, dated Apr. 3, 2019, 2 pages.

* cited by examiner

METHODS AND DEVICES FOR SANITATION, DISINFECTION AND STERILIZATION

PRIORITY

This application is national filing of international application PCT/US2016/042183 filed on Jul. 14, 2016 and claiming priority of U.S. provisional application No. 62/192,324 filed on Jul. 14, 2015, the contents of both of which are incorporated herein by reference.

FIELD OF THE INVENTION

The present invention relates to methods and devices used to sanitize, disinfect and sterilize areas, spaces, surfaces and items as well as to sanitize human skin. More specifically the invention relates to methods and devices used to sanitize, disinfect and sterilize areas, spaces, surfaces and items as well as to sanitize hands and feet by using near infrared (NIR) illumination optionally with other wavelengths and other treatments such as ozone. The methods and devices will be of major importance to the healthcare industry and to other industries or physical environments that require sanitizing, disinfecting or sterilizing.

BACKGROUND OF THE INVENTION

It is well known that various types of microbial infections may be spread in public places. Institutions such as hospitals, nursing homes, schools, daycare centers, extended care facilities etc. are especially prone to the spread of bacterial and viral infections. In health-care and clinical settings, microbial infections are specifically problematic on one hand due to the need for a clean environment for medical procedures and on the other hand due to the weakened immune systems of patients. For this reason, sanitation, disinfection and sterilization protocols in hospitals are very strict. However, current methods have certain drawbacks: various microbes have become resistant to a number of chemicals, some chemicals are allergens, human skin is susceptible to certain chemicals, some methods require long treatment times, and so on.

Further problems arise from the fact that there are many different types of health-care equipment and what fails in the disinfection or sterilization process is always different. For example, it has been found that many private endoscopy clinics used poor sterilization methods for nearly a decade. The World Health Organization (WHO) estimates that at any point in time, more than 1.4 million people worldwide are affected by infections acquired in hospitals. Between 5% and 10% of patients admitted to modern hospitals in the developed world acquire one or more healthcare-associated infections. The Centers for Disease Control and Prevention (CDC) estimate that approximately 1.7 million healthcare-associated infections occur annually in the U.S. and that they are associated with nearly 100,000 deaths each year. Health-care-associated infections are also an important problem in extended care facilities, including nursing homes and rehabilitation centers. Also, antibiotic resistant bacteria that cannot be controlled or killed by antibiotics like Methicillin-resistant *Staphylococcus aureus* (MRSA or golden staph), vancomycin-resistant *Enterococcus* (VRE) and multi-drug-resistant *Mycobacterium tuberculosis* (MDR-TB) are serious public health threats.

Methods to diminish and eliminate microbes in healthcare facilities include hand washing, surface cleaning, use of antimicrobial agents, and sterilization by chemicals, heat, or steam.

The use of UV light has been known and accepted in industrial applications for a long time. UV light has been used to sterilize hospital environments. UV light has also been introduced to purify water. WO2005031881 describes UV light usage for water purification and also indicates that UV light-emitting diodes may be used.

The use of UV light in food preservation is also known. U.S. Pat. No. 6,030,653 discloses a combination of UV light with visible light and pulsed NIR light (950 nm) for diminishing iron-dependent bacteria, such as *E. coli* and *Salmonella* in food products. The patent shows a log 1.5 reduction of *E. coli* upon illumination with visible and pulsed NIR.

UV light in combination with ozone has been shown to efficiently kill *Listeria bacterium* in fresh brine.

Ozone has been also shown to kill airborne microbes in dental clinics for example. Ozone has also been shown to reduce foodborne *E. coli* and *Listeria* colonies in leafy salads.

Accordingly, there are various methods to reduce microbial infections. However, specifically in health-care environments, it is not enough to reduce the microbial population to a certain amount; the microbial population has to be eliminated. Even the smallest amounts of microbes in health-care environments may be detrimental.

Moreover, methods such as UV light cannot be used in every situation given that it does not penetrate rather it affects only the surface. Moreover, UV is toxic for human tissues and cannot be used everywhere and all the time.

Therefore, there is a need for safe, non-toxic and easy-to-use methods for disinfection and sterilization of areas and devices in health-care settings. This invention provides novel and non-obvious solutions to be applied in various areas of the healthcare industry and other industries or physical environments that require sanitizing, disinfecting or sterilizing.

SUMMARY OF THE INVENTION

Accordingly it is an object of this invention to provide methods and devices for sanitizing, disinfecting and sterilizing areas, spaces, surfaces and items as well as to sanitize hands and feet.

It is an object of this invention to provide a device for diminishing microorganisms, said device comprising one or more LED elements emitting NIR light in a wavelength range of 750-960 nm; optionally one or more OLED elements emitting NIR light wavelengths within a range of 750 to 800 nm; optionally additional LED elements emitting visible light within a range of 380 to 475 nm and of wavelengths within a range of 500-700 nm; optionally the addition of one or more OLED elements emitting visible light within the range of 380 to 475 nm and 500 to 700 nm, and optionally additional LED elements emitting UV-C light with wavelengths within a range of 240 to 260 nm.

It is an object of this invention to provide a device for diminishing microorganisms, said device comprising one or more LED or OLED elements emitting NIR, UV-C and visible light and the number of LEDs and/or OLEDs emitting NIR and UV-C lights is larger than the number of LED and/or OLED elements emitting visible light.

It is another object of this invention to provide a device for diminishing microorganisms, said device comprising one or more LED or OLED elements emitting NIR, UV-C and visible lights, wherein the UV-C LEDs can be switched on and off separately from the other LEDs and OLEDs and optionally automatically when a sensor has detected an event indicating the presence of a human being.

It is an object of this invention to provide a device for diminishing microorganisms, said device comprising one or more LED or OLED elements emitting NIR, UV-C and visible lights and an ozone generator.

It is an object of this invention to provide a device for personal hygiene use in public facilities and areas, a device that would diminish number of microorganisms on human skin.

It is an object of this invention to provide a device capable of diminishing number of microorganisms within one to sixty minutes.

It is an object of this invention to provide a device capable of eradicating bacteria, viruses, fungi and parasites within one to sixty minutes.

It is an object of this invention to provide a device capable of eradicating MSRA and *C. difficile* within one to sixty minutes.

It is yet another object of this invention to provide a device capable of sterilizing certain hospital areas, such as surgery rooms.

It is still another object of this invention to provide a container or a box for either disinfecting or sterilizing items, where LED and/or OLED elements emitting NIR, UV-C and visible light are located inside the device.

Another object of this invention is to provide a medical tray where LED and/or OLED elements emitting NIR, UV-C and visible light either disinfect or sterilize medical instruments inside the tray.

It is a further object of this invention to provide a method for disinfecting an area, said method comprising illumination of the area with one or more LED elements emitting NIR light of a wavelength within a range of 750 to 960 nm continuously for five to 50 minutes.

Another object of the invention is to provide a method for sterilizing an area, said method comprising illumination of the area with one or more LED elements emitting NIR light of a wavelength within a range of 750 to 960 nm and one or more LED elements emitting UV-C light of a wavelength within a range of 240 to 260 nm; one or more LED elements emitting light of a wavelength within a range of 380 to 475 nm (UV-A, violet and blue light); one or more LED or OLED elements emitting light of a wavelength within a range of 475 to 700 nm wherein all LED elements are on a low profile aluminum strip on which is aligned a series of these LEDs of different wavelengths.

It is a further object of the invention to provide a method for disinfecting or sterilizing an area by illuminating with one or more LED elements emitting NIR, UV-C, and visible light, and where UV-C LEDs can be switched off separately from the other LEDs or OLEDs and optionally where UV-C LEDs are automatically switched off when a detector recognizes an event indicating a human being is present in the area.

An object of the invention is to provide a method for sterilizing an area by illuminating with one or more LED elements emitting NIR, UV-C, and visible light and additionally includes providing an ozone stream in the area.

Yet another object of this invention is to provide a device for sanitizing human skin, said device comprising: a housing having one or more LED-strips comprising one or more LED and/or OLED elements emitting NIR light of a wavelength within a range of 750 to 960 nm wherein the housing is adapted to accept one or more human hands or feet to be exposed to the NIR light.

BRIEF DESCRIPTION OF THE FIGURES

FIG. 6A-D.

DETAILED DESCRIPTION OF THE INVENTION

Definitions

By infrared it is meant wavelengths above 1400 nm.
By near infrared (NIR) it is meant wavelengths 750-1400 nm.
By visible light it is meant wavelengths 390-750 nm.
By photosynthetically active radiation (PAR) it is meant wavelengths 400-700 nm.
By blue light it is meant wavelengths 380-495 nm.
By ultraviolet light it is meant wavelengths 10-380 nm.
By ultraviolet C light it is meant wavelengths 100-290 nm.
By ultraviolet A light it is meant wavelengths 350-400 nm.
By orange light it is meant wavelengths 590-620 nm.
By red light it is meant wavelengths 600-700 nm.
By far red light it is meant wavelengths 700-750 nm.

By green light it is meant wavelengths 495-590 nm.

By yellow light it is meant wavelengths 570-590 nm.

By cool white light it is meant the light with correlated color temperatures* of 5000-6000K.

*Correlated Color temperature (CCT) in lighting describes how the color of the light appears from a lamp, measured in Kelvins (K).

By warm white light it is meant the light with correlated color temperatures of 2700-3500K.

In the present context, the terms 'LED', 'LED element' and 'light-emitting diode' are used interchangeably and refer to light-emitting diodes in all known forms, be it inorganic, organic, point-like, or line-like. In one embodiment, the LEDs are wide-angle elements, which refer to LEDs which deliver light evenly on the illuminated surface. The LEDs may be used in high-power output and emit continuously.

By OLED it is meant organic light-emitting diode. OLED is a light-emitting diode (LED) in which the emissive electroluminescent layer is a film of organic compound which emits light in response to an electric current.

The words "eradicating" and "sterilizing" are used synonymously and what is meant is a decrease of infection-causing microbes by at least a log 5 reduction level.

By "disinfecting" it is meant a decrease of infection-causing microbes by at least a log 4 reduction level.

By "sanitizing" it is meant a decrease of infection-causing microbes by at least a log 2 reduction level.

The present invention relates to methods for either disinfecting or sterilizing an area, devices, or garments and fabrics. Certain embodiments relate to sanitizing human skin, especially hands or feet. The methods comprise providing a light system capable of illuminating an area, a device, set of devices, garments and fabrics, or human skin, with near infrared light from several light-emitting diodes, optionally in combination with violet, blue or ultraviolet (UV) lights. The method may comprise additionally the use of ozone to achieve further reduction of infection-causing microbes. In an embodiment where the illumination is used to sanitize human skin, UV light is not applied.

Moreover, the present invention relates to a method to turn all or part of the illumination and/or ozone generation off automatically when human skin may be exposed.

The method and device of this invention are unique in their ability to eradicate (at least 5 log reduction and preferably 6 log reduction i.e. 99.9999%) all kinds of bacteria (both Gram-positive and Gram-negative), fungi, viruses and pathogenic protozoa in a short period of time (from 5 to 20 minutes).

The method and device can be used to eradicate bacteria in at least the following genus: *Chlamydia, Clostridium, Escherichia, Helicobacterium, Lactobacillus, Legionella, Leuconostoc, Listeria, Pediococcus, Salmonella, Shigella, Staphylococcus, Vibrio* and *Yersinia*. The method and device may be used to eradicate other bacterial genus as well. Specifically, the method and device can be used to eradicate MSRA and *C. difficile*.

The method and device can be used to eradicate fungi in at least the following genus: *Aspergillus, Penicillium, Saccharomyches* and *Candida*. The method and device may be used to eradicate other fungal species as well.

The method and device can be used to eradicate parasites in at least the following genus: *Amoeba, Cryptosporium* and *Giardia*. The method and device may be used to eradicate other parasites as well.

The method and device can be used to eradicate viruses in at least the following genus and groups: Rotavirus, Norovirus, Human papilloma virus, Herpes virus, Hepatitis virus, Influenza virus and HIV. The method and device may be used to eradicate other viruses as well.

According to this invention the synergistic effects of combinations of NIR with UV-C, ozone and/or ionized silver provide the fastest (from 5 to 20 minutes) and greatest (99.9999 or 6 log reduction of cfu) killing effect of any combination of bacterial, fungal and virus populations.

Effects of Ozone on Specific Bacteria, Virus and Molds.

Ozone ($O_3$) is a gas and an unstable form of oxygen ($O_2$) and has a total of three atoms, unlike stable oxygen that has only two atoms. In nature, ozone is formed by the sun's ultraviolet rays and the high-energy electrical discharges that happen during lightning storms.

Ozone can also be reproduced scientifically in safe, controlled quantities. Ozone continuously applied in slightly elevated concentrations is an extremely effective, safe and economical method of reducing common bacteria, yeasts, molds, mildew and viruses on surfaces in homes, public places and in the air we breathe. By oxidizing the by-products of decay, ozone rapidly eliminates the allergens from dust mites and other arthropods. Ozone can also eliminate harmful chemical gases that are emitted from plywood, carpet, glue, paint, many indoor cleaners, etc. Ozone's powerful oxidizing action quickly reduces trapped chemical residues to harmless by-products. Ozone interferes with the metabolism of bacterium-cells, most likely through inhibiting and blocking the operation of the enzymatic control system. A sufficient amount of ozone breaks through the cell membrane, and this leads to the destruction of the bacteria.

Viruses are small, independent particles, built of crystals and macromolecules. Ozone destroys viruses by diffusing through the protein coat into the nucleic acid core, resulting in damage of the viral RNA.

As a comparison based on 99.99% of bacterial concentration being killed and time taken, ozone is 25 times more effective than HOCl (Hypochlorous Acid); 2,500 times more effective than OCl (Hypochlorite); and 5,000 times more effective than $NH_2Cl$ (Chloramine).

TABLE 1

The effects of ozone on various bacterial, viral and fungal species. The results are from published literature.

| Pathogen | Dosage |
| --- | --- |
| *Aspergillus Niger* (Black Mount) | Destroyed by 1.5 to 2 mg/l |
| *Bacillus* Bacteria | Destroyed by 0.2 m/l within 30 seconds |
| *Bacillus Anthracis* (causes anthrax in sheep, cattle and pigs. Also a human pathogen) | Ozone susceptible |
| *Bacillus cereus* | 99% destruction after 5-min at 0.12 mg/l in water |

TABLE 1-continued

The effects of ozone on various bacterial, viral and fungal species. The results are from published literature.

| Pathogen | Dosage |
| --- | --- |
| *B. cereus* (spores) | 99% destruction after 5-min at 2.3 mg/l in water |
| *Bacillus subtilis* | 90% reduction at 0.10-PPM for 33 minutes |
| Bacteriophage f2 | 99.99% destruction at 0.41 mg/l for 10-seconds in water |
| *Botrytis cinerea* | 3.8 mg/l for 2 minutes |
| *C. difficile* | 99.999% destruction at 0.6 mg/l for 2 minutes (in water) |
| *Candida* Bacteria | Ozone susceptible |
| *Clavibacter michiganense* | 99.99% destruction at 1.1 mg/l for 5 minutes |
| *Cladosporium* | 90% reduction at 0.10-PPM for 12.1 minutes |
| *Clostridium* Bacteria | Ozone susceptible |
| *Clostridium Botulinum* Spores. Its toxin paralyses the central nerve system, being a poison multiplying in food and meals. | 0.4 to 0.5 mg/l threshold value |
| Coxsackie Virus A9 | 95% destruction at 0.035 mg/l for 10-seconds in water |
| Coxsackie Virus B5 | 99.99% destruction at 0.4 mg/l for 2.5-minutes in sludge effluent |
| Diphtheria Pathogen | Destroyed by 1.5 to 2 mg/l |
| Eberth *Bacillus* (Typhus abdomanalis). Spreads typically by aqueous infection and causes typhoid. | Destroyed by 1.5 to 2 mg/l |
| Echo Virus 29: The virus most sensitive to ozone. | After a contact time of 1 minute at 1 mg/l of ozone, 99.999% killed. |
| Enteric virus | 95% destruction at 4.1 mg/l for 29 minutes in raw wastewater |
| *Escherichia Coli* Bacteria (from feces) | Destroyed by 0.2 mg/l within 30 seconds in air |
| E-coli (in clean water) | 99.99% destruction at 0.25 mg/l for 1.6 minutes |
| E-coli (in wastewater) | 99.9% destruction at 2.2 mg/l for 19 minutes |
| Encephalomyocarditis Virus | Destroyed to zero level in less than 30 seconds with 0.1 to 0.8 mg/l. |
| Endamoebic Cysts Bacteria | Ozone susceptible |
| Enterovirus Virus | Destroyed to zero level in less than 30 seconds with 0.1 to 0.8 mg/l. |
| *Fusarium oxysporum* f.sp. *lycopersici* | 1.1 mg/l for 10 minutes |
| *Fusarium oxysporum* f.sp. *melonogea* | 99.99% destruction at 1.1 mg/l for 20 minutes |
| GDVII Virus | Destroyed to zero level in less than 30 seconds with 0.1 to 0.8 mg/l. |
| Hepatitis A virus | 99.5% reduction at 0.25 mg/l for 2-seconds in a phosphate buffer |
| Herpes Virus | Destroyed to zero level in less than 30 seconds with 0.1 to 0.8 mg/l. |
| Influenza Virus | 0.4 to 0.5 mg/l threshold value |
| Klebs-Loffler *Bacillus* | Destroyed by 1.5 to 2 mg/l |
| *Legionella pneumophila* | 99.99% destruction at 0.32 mg/l for 20 minutes in distilled water |
| *Luminescent Basidiomycetes* (species having no melanin pigment). | Destroyed in 10 minutes at 100-PPM |
| *Mucor piriformis* | 3.8 mg/l for 2 minutes |
| *Mycobacterium avium* | 99.9% with a CT value of 0.17 in water (scientifically reviewed document) |
| *Mycobacterium foruitum* | 90% destruction at 0.25 mg/l for 1.6 minutes in water |
| *Penicillium* Bacteria | Ozone susceptible |
| *Phytophthora parasitica* | 3.8 mg/l for 2 minutes |
| Poliomyelitis Virus | 99.99% kill with 0.3 to 0.4 mg/l in 3-4 minutes |
| Poliovirus type 1 | 99.5% destruction at 0.25 mg/l for 1.6 minutes in water |
| *Proteus* Bacteria | Very susceptible |
| *Pseudomonas* Bacteria | Very susceptible |
| Rhabdovirus virus | Destroyed to zero level in less than 30 seconds with 0.1 to 0.8 mg/l |
| *Salmonella* Bacteria | Very susceptible |
| *Salmonella typhimurium* | 99.99% destruction at 0.25 mg/l for 1.67 minutes in water |
| *Schistosoma* Bacteria | Very susceptible |
| *Staph epidermidis* | 90% reduction at 0.1-ppm for 1.7 min |
| Staphylococci | Destroyed by 1.5 to 2.0 mg/l |
| Stomatitis Virus | Destroyed to zero level in less than 30 seconds with 0.1 to 0.8 mg/l |

TABLE 1-continued

The effects of ozone on various bacterial, viral and fungal
species. The results are from published literature.

| Pathogen | Dosage |
| --- | --- |
| *Streptococcus* Bacteria | Destroyed by 0.2 mg/l within 30 seconds |
| *Verticillium dahliae* | 99.99% destruction at 1.1 mg/l for 20 minutes |
| Vesicular Virus | Destroyed to zero level in less than 30 seconds with 0.1 to 0.8 mg/l |
| Virbrio Cholera Bacteria | Very susceptible |

The effect of ozone below a certain critical concentration value is small or zero. Above this level all pathogens are eventually destroyed. This effect is called all-or-none response and the critical level is the "threshold value". According to this invention the "threshold value" of ozone is reduced by applying ozone simultaneously with NIR exposure and optionally with UV wavelengths. The surprising result of the method of this invention is the synergistic effect of the light treatment and ozone.

Antimicrobial Effects of Ionized Silver.

The antimicrobial properties of silver have been known to cultures all around the world for many centuries. The Phoenicians stored water and other liquids in silver coated bottles to discourage contamination by microbes. Silver dollars used to be put into milk bottles to keep milk fresh and water tanks of ships and airplanes that are "silvered" are able to render water potable for months. In 1884 it became a common practice to administer drops of aqueous silver nitrate to newborn's eyes to prevent the transmission of *Neisseria gonorrhoeae* from infected mothers to children during childbirth.

Once antibiotics were discovered, the use of silver as a bactericidal agent decreased. However, with the discovery of antibiotics came the emergence of antibiotic-resistant strains such as CA-MRSA and HA-MRSA, the flesh-eating bacteria.

In order for silver to have any antimicrobial properties, it must be in its ionized form. Silver in its non-ionized form is inert, but contact with moisture leads to the release of silver ions Thus, all forms of silver or silver containing compounds with observed antimicrobial properties are in one way or another sources of silver ions (Ag+); these silver ions may be incorporated into the substance and released slowly with time as with silver sulfadiazine, or the silver ions can come from ionizing the surface of a solid piece of silver as with silver nanoparticles. Silver zeolite is also a commonly used form of antibacterial silver.

Various types of food packaging have been supplemented with silver-containing compounds to deter microbial growth and extend product shelf life.

According to this invention NIR illumination may be used in combination with UV light, ozone and/or ionized silver. Table 2 below illustrates the advantages and drawbacks of each of these methods and benefits of these in various combinations.

TABLE 2

The benefits of using NIR and UV in combination with ozone and ionized silver.

| Microbial killing factors and their combinations | Effects on microorganisms |
| --- | --- |
| NIR (750-950 nm) | 80% to 99.9% or 2-3 log reduction of the iron-dependent and some other types of bacteria and fungi. |
| UV-C | Kills microbes mostly on the surface of the products, in air or in light transparent water due to lack of penetration of UV light through most of the materials. |
| Ozone | Kills from 90% to 99.99% of microbes. For example, ozone destroys 99.9% at 2.2 mg/l for 19 minutes. |
| Ionized silver | It was found that silver has the most effective antibacterial action and the least toxicity to animal cells. Due to increasing antibiotic resistance, there has recently been a renewed interest in using silver as an antibacterial agent. |
| NIR + UV-C | NIR + UV-C combination is more effective in eliminating microbes and viruses compared to either factor working alone. |
| NIR + Ozone | NIR + Ozone combination is more effective in eliminating microbes and viruses compared to either factor working alone. Ozone in a concentration of 0.02 PPM in a moderately humid atmosphere exercises a very definite killing effect against bacteria on surfaces, but below this level it has little effect. A combination of ozone with NIR makes ozone efficient in killing bacteria at low concentrations (around 0.01 PPM and even less). |
| UV-C + Ozone | UV-C + Ozone combination is more effective in eliminating microbes and viruses compared to either factor working alone. A synergistic effect of UV-C and ozone has been reported on the disinfection of water. The combination of low-dose ozone with UV irradiation is an option to give the benefit of disinfection and to reduce drawbacks of UV and ozone disinfection. (Jingyun FANG, Huiling LIU, Chii SHANG, Minzhen ZENG, Mengling NI, Wei LIU. *E. coli* and bacteriophage MS2 disinfection by UV, ozone and the combined UV and ozone processes. Front. Environ. Sci. Eng. 2014, 8(4): 547-552) |

TABLE 2-continued

The benefits of using NIR and UV in combination with ozone and ionized silver.

| Microbial killing factors and their combinations | Effects on microorganisms |
|---|---|
| UV-C + Ionized silver | UV-C + Ionized silver combination is more effective in eliminating microbes and viruses compared to either factor working alone. |
| NIR + Ionized silver | NIR + Ionized silver combination is more effective in eliminating microbes and viruses compared to either factor working alone |
| NIR + UV-C + Ozone and/or Ionized silver | This multiple combination is able to completely eradicate almost all types and species of microbes (killing rate is 99.999% and higher within a very short period of time (e.g. 5 minutes). Also, the combination is more effective in eliminating antibiotic resistant bacteria like MRSA. |

Figure 1:
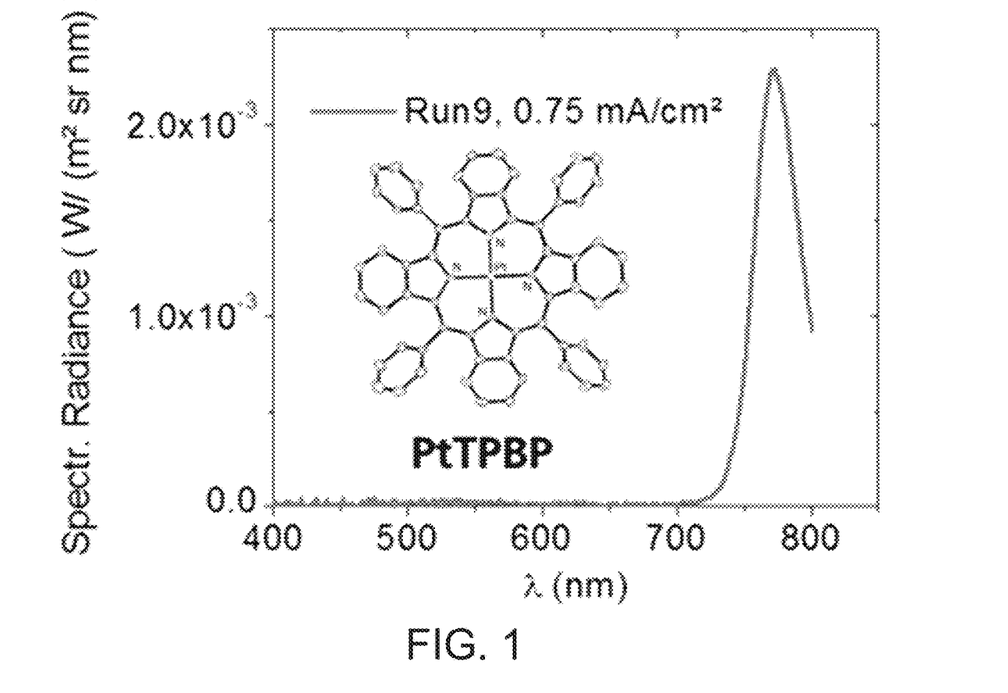
FIG. 1 illustrates a peak at about 771 nm of an OLED light.
Figure 2:
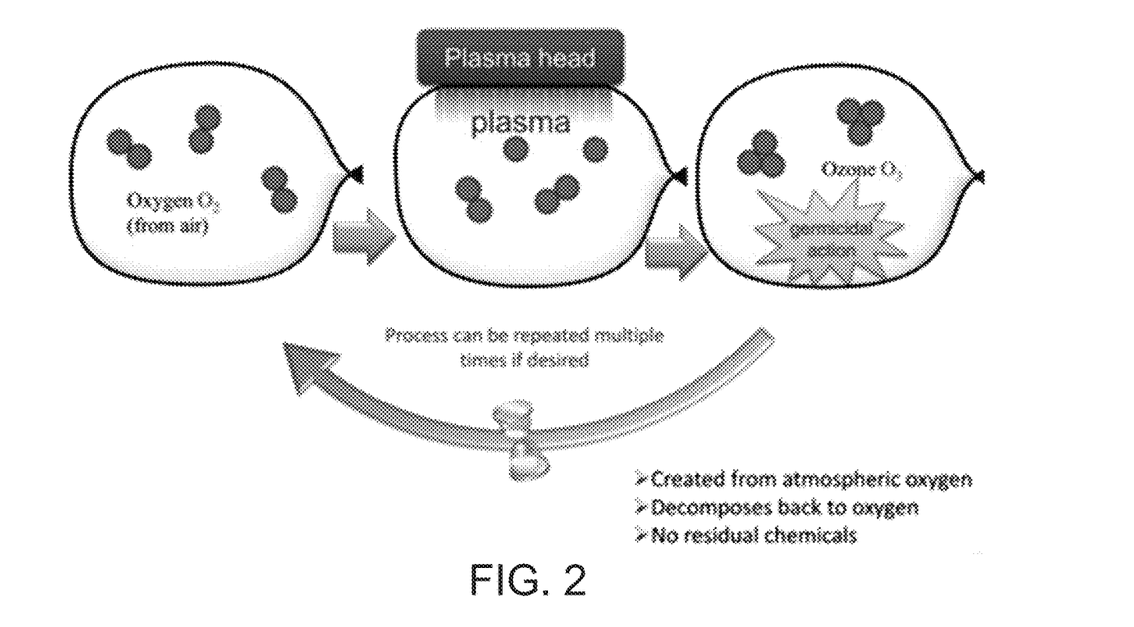
FIG. 2 illustrates the germicidal action of ozone.
Figure 3:
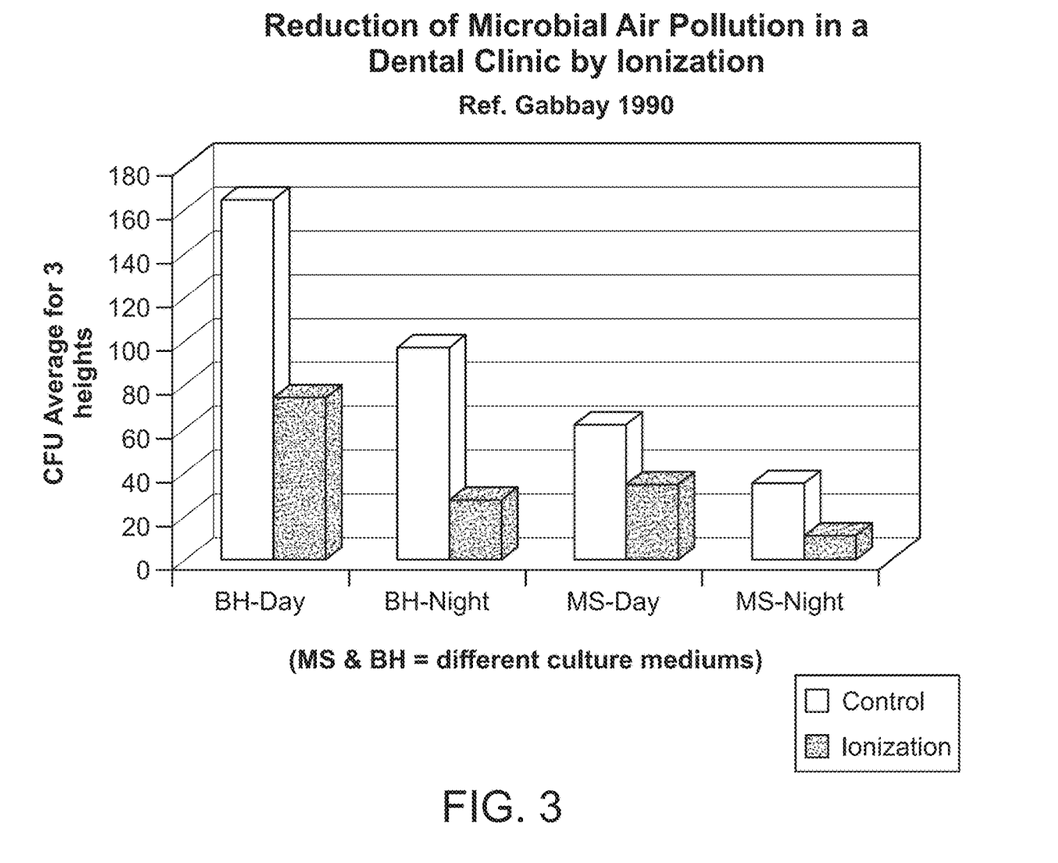
FIG. 3 illustrates the reduction of microbial air pollution in a clinic by ionization. Adapted from Gabbay, J. (1990). "Effect of ionization on microbial air pollution in the dental clinic." Environ. Res. 52(1): 99.
Figure 4:
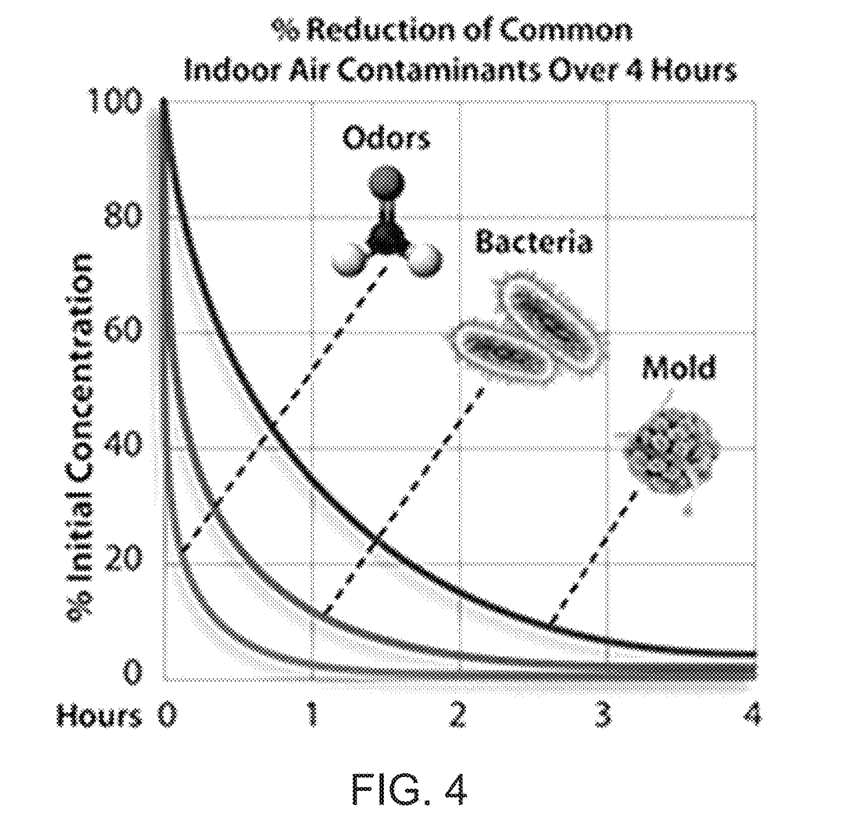
FIG. 4 illustrates the effect of UV-C light on common household contaminants: odors, bacteria and mold.
Figure 5:
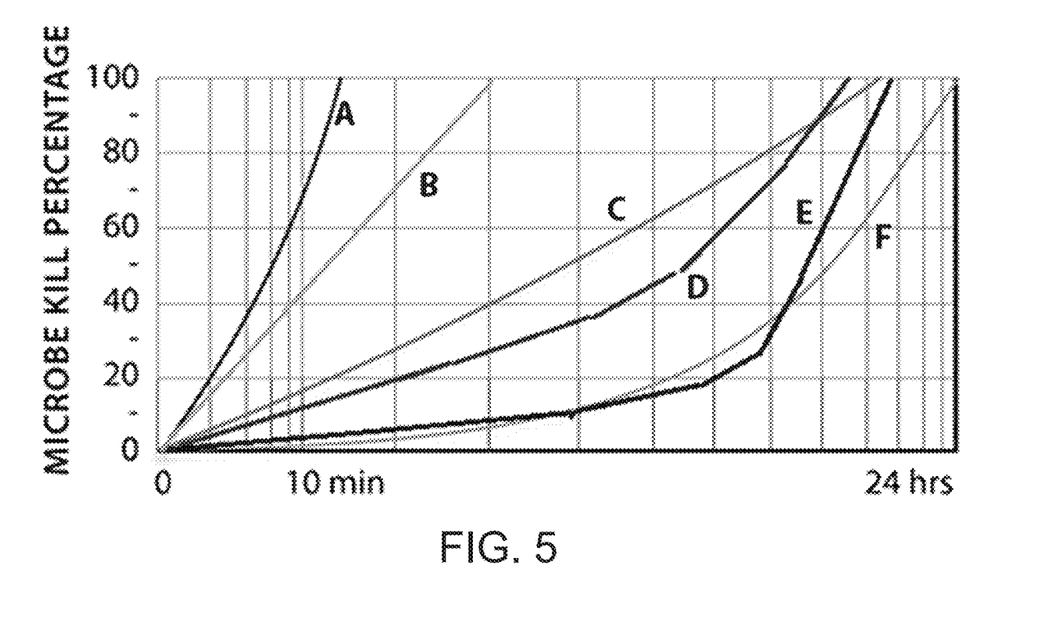
FIG. 5 illustrates the synergistic effect of NIR and other methods of this disclosure. E is the application of NIR of 850-890 nm and 920-960 nm. B is a combination of NIR with UV-C. D is a combination of NIR with ozone. The C curve is related to UV-C treatment, F is ozone treatment and A is a combination of NIR with UV-C and ozone. The combination: NIR+UV-C and ozone provided the fastest (from 10 to 20 minutes) and greatest (99.99999 or 7 log reduction of cfu) killing effect or eradication of *Bacillus subtilis*.
Figure 6A:
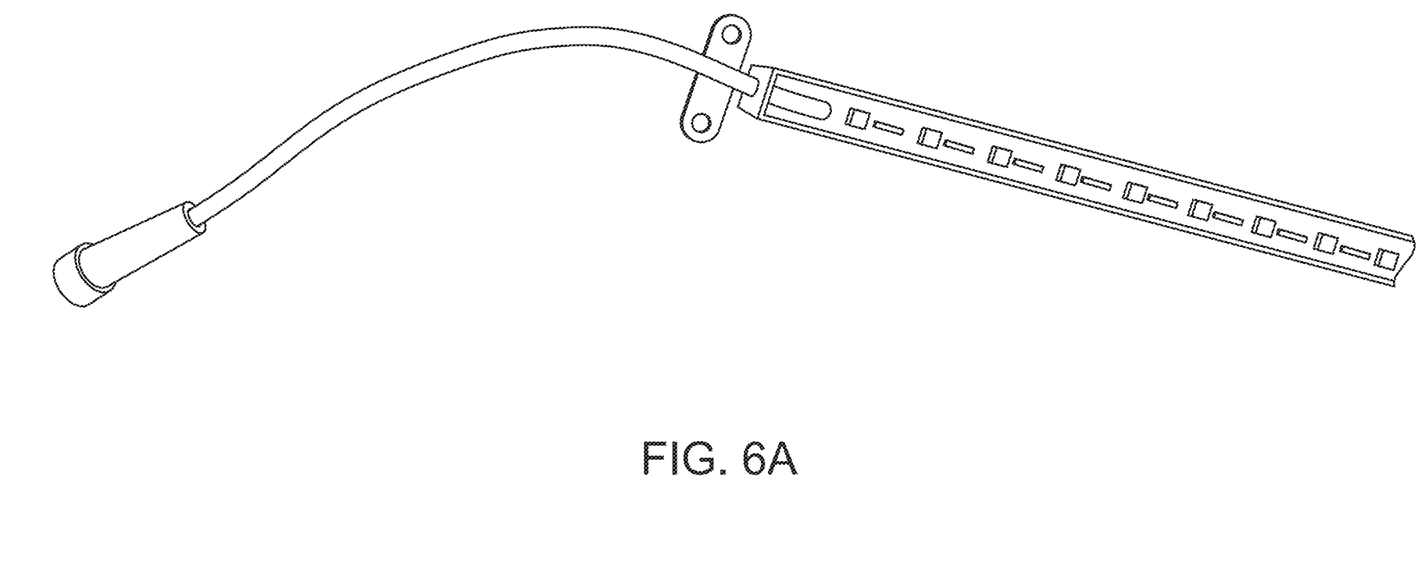
FIG. 6A shows LED strips of NIR wavelengths of 850-890 nm, UV-C of 260 nm, violet light of 405 nm and blue light of 425 nm and a LED panel assembled from these strips of various colors (wavelengths).
Figure 6B:
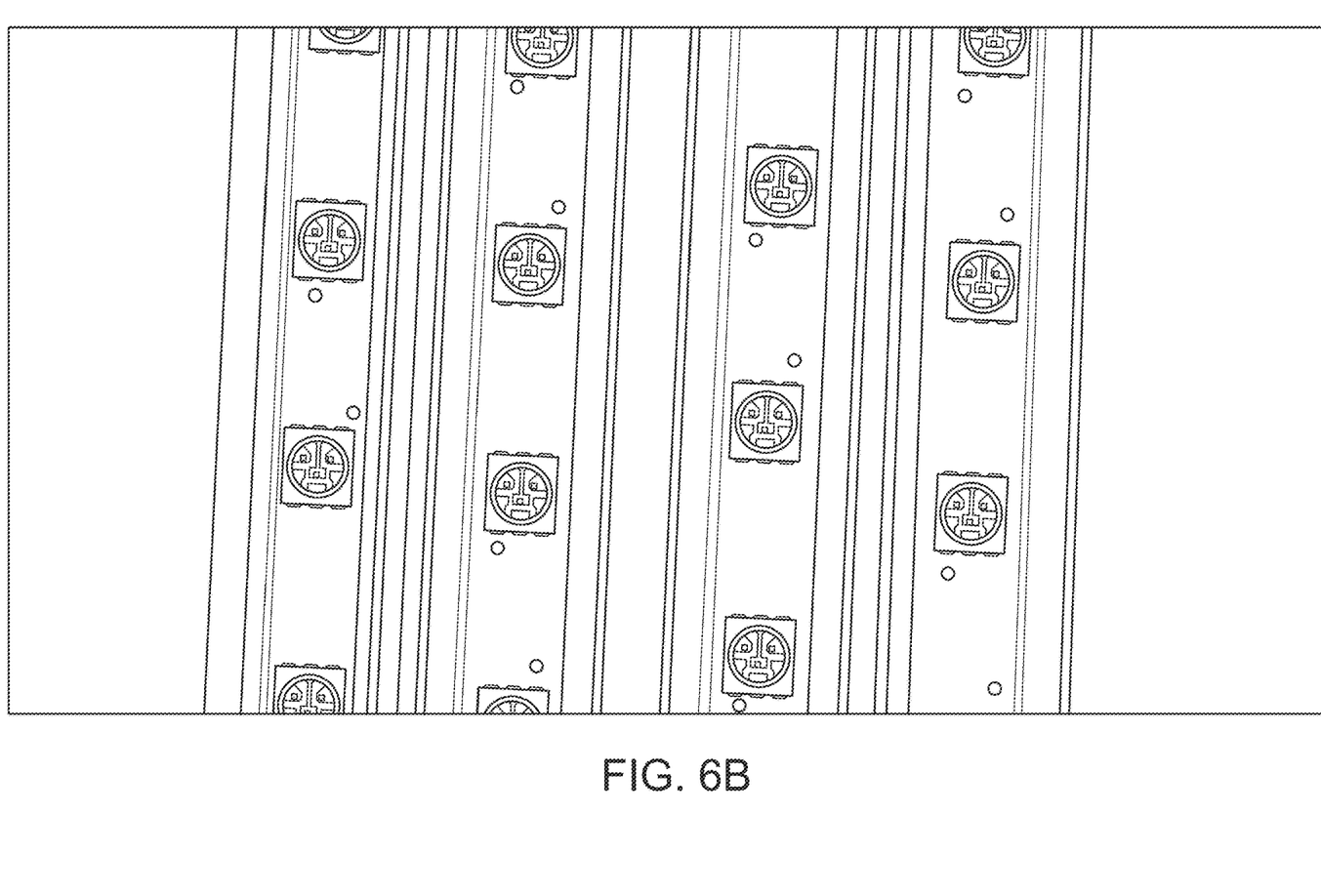
FIG. 6B shows a single LED emitter.
Figure 6C:
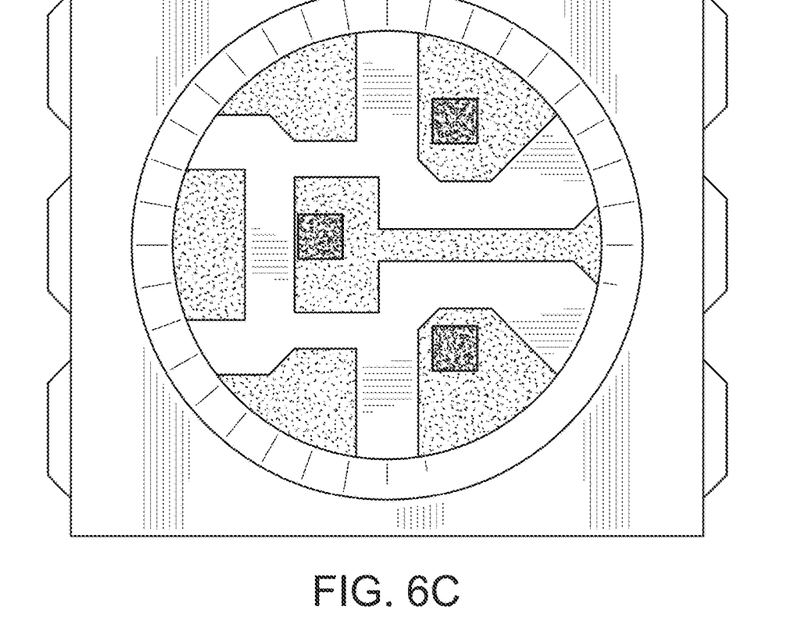
FIG. 6C shows a single 5050 SMD infrared LED emitter of 850 nm.
Figure 6D:
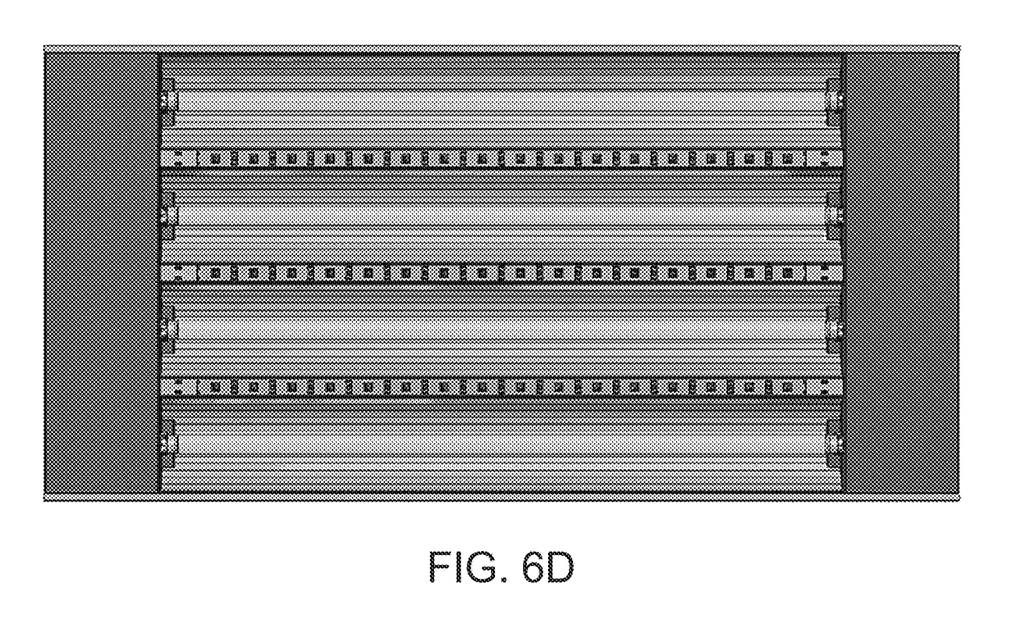
FIG. 6D. shows a variation of Steril MAX lighting system in a rectangular shaped unit consisting of a metal (optionally aluminum) case with 3 strips of NIR LED emitters with 16 emitters in each strip (48 LED emitters as total per unit), 4 UV-C tubes and a power supply. Steril MAX can achieve a high level of microbial reduction with a mix of near infrared and ultraviolet lights. The unit is designed to be portable and sensitive to motion ensuring safe operation given the UV-C.

The synergistic effect of a combination of NIR with UV-C, ozone and/or ionized silver is illustrated in FIG. 5, where E is the application of NIR of 850-890 nm and 920-960 nm. B is a combination of NIR with UV-C. D is a combination of NIR with ozone. The C curve is related to UV-C treatment, F is ozone treatment and A is a combination of NIR with UV-C and ozone. The combination NIR+UV-C and ozone provided the fastest (from 10 to 20 minutes) and the greatest (99.9999% or 6 log reduction of cfu) killing effect on *Bacillus subtilis*.

The invention of this disclosure is now described by means of non-limiting examples. A skilled artisan will recognize that various modifications may be made without dividing from the spirit of the invention.

Example 1

Sterilizing a Surgery Room

The Vitabeam™ Steril MAX consists of a high bay on which the original LEDs are replaced by a mix of UV-C & NIR wavelengths. This product is meant to be used as a prototype to determine the optimal light output required to kill MRSA and other microbes.

According to a preferred embodiment the LED lights provide NIR wavelengths selected from the group consisting of: 800-850 nm, 850-880 nm, 880-900 nm, 900-930 nm and 930-970 nm (950 max) and combinations thereof from 1 to 100 Watts/m². The UV-C-wavelength is preferably 250-260 nm. According to one preferred embodiment the LED lights additionally provide blue light. Blue light wavelengths are preferably between 405 and 425 nm. A combination of these wavelengths provides the highest possible destruction of both iron-dependent and non-iron dependent bacteria.

According to one preferred embodiment the lamp comprises OLED (organic light emitting diodes) emitting in the range of 750-820 nm.

According to one preferred embodiment, one lamp is installed per 3-4 cubic meter of area. Depending on what level of microbial reduction is required, the number of lamps per cubic area may vary. According to a preferred embodiment for particular uses in hospitals for example, the number of lamps per cubic area is such that a decrease of microbes at 5 log level reduction is achieved in ten minutes or less. The number of lamps per cubic area may be from 1-10 per cubic meter, more preferably 2-5 and most preferably 2-3.

The Vitabeam™ Steril MAX (production version) will be installed in specific hospital areas where MRSA and other microbes are identified as being a risk to human beings. The lamp is to be installed on the ceiling, in the middle of the room. Due to the harmful effects of UV-C on human skin, this lamp will be used only for a limited period of time when humans are not within its operating area. According to one preferred embodiment, the UV light is turned off automatically upon indication of a human being entering the space. For example, opening a door may trigger the system to turn the UV light off. Alternatively, the UV light may turn on only at certain pre-determined times, for example during night hours.

According to one embodiment, the light may be connected to an ozone generator such that in addition to the light, the system provides ozone flow in the area. The ozone generator may be connected to the same regulation system as the UV light, thereby providing ozone flow only when human beings are not present.

Example 2

Effect of Vitabeam™ Steril MAX Light on *Staphylococcus aureus*, MSRA (Methicillin-Resistant *Staphylococcus aureus*), *Escherichia coli* (*E. coli*) and *Salmonella typhimurium*

The experiments were conducted to evaluate the most effective combination of the wavelengths to eradicate *Staphylococcus aureus*, MSRA, *Escherichia coli* (*E. coli*) and *Salmonella typhimurium*. The experiments were conducted by exposing bacterial colonies on Petri dishes to different wavelength combination for different periods of time. The area of the colonies is evaluated before and after the illumination. The experiments were conducted under ambient atmosphere and temperature. The results were at least 99.9994% (5-log) reduction in 30 seconds and almost complete eradication 99.9999%-100% reduction (6-7 log and higher) in 30 minutes of irradiation of bacterial colonies with Vitabeam™ Steril MAX lighting, comprising illumination with wavelengths at the following ranges: 800-1000 nm, 400-450 nm and 250-400 nm. The NIR wavelengths may be selected from the groups consisting of: 800-850 nm, 850-860 nm, 860-880 nm, 880-900 nm, and 930-970 nm. The synergistic effect of a combination of NIR with UV-C resulted in the highest possible log reduction in such a short period of irradiation as 30 seconds. Tables 4, 5, 6 and 7:

TABLE 4

Efficacy of the Vitabeam ™ Steril MAX unit
against *Staphylococcus aureus* at 30-min treatments.
The illumination included wavelengths 240-260 nm and 800-960 nm.

| Replicate | Time zero Population CFU/mL | 30-minute Treatment Population CFL/mL |
|---|---|---|
| 1 | $9.20 \times 10^6$ | $1.00 \times 10^1$ |
| 2 | $7.50 \times 10^6$ | $1.00 \times 10^1$ |
| 3 | $6.70 \times 10^6$ | $2.00 \times 10^1$ |
| Average | $7.80 \times 10^6$ | $1.33 \times 10^1$ |
| Log Reduction | | 5.7879 |
| % Reduction | | 99.9998 |

TABLE 5

Efficacy of the Vitabeam ™ Steril MAX unit against MRSA
bacteria at 30-min treatments. The illumination included
wavelengths at 240-260 nm and 800-960 nm.

| Replicate | Time zero Population CFU/mL | 30-minute Treatment Population CFU/mL |
|---|---|---|
| 1 | $6.40 \times 10^7$ | $1.00 \times 10^1$ |
| 2 | $9.90 \times 10^7$ | $1.00 \times 10^1$ |
| 3 | $4.60 \times 10^7$ | $1.00 \times 10^1$ |
| Average | $6.97 \times 10^7$ | $1.00 \times 10^1$ |
| Log Reduction | | 6.8215 |
| % Reduction | | 99.9999 |

TABLE 6

Efficacy of the Vitabeam ™ Steril MAX unit against
*Escherichia coli* at 30-second treatments. The illumination
included wavelengths at 240-260 nm and 800-960 nm.

| Replicate | Initial Population | T-30 sec | Log Reduction | % Reduction |
|---|---|---|---|---|
| 1 | 2.30E+07 | 5.00E+01 | 5.66 | 99.9998 |
| 2 | 8.90E+07 | 2.00E+01 | 6.65 | 100.0000 |
| 3 | 3.24E+07 | 2.00E+01 | 6.21 | 99.9999 |
| Average | 4.81E+07 | 3.00E+01 | 6.1735 | 99.9999 |

TABLE 7

Efficacy of the Vitabeam ™ Steril MAX unit against
*Salmonella typhimurium* at 30-sec treatments. The illumination
included wavelengths at 240-260 nm and 800-960 nm.

| Replicate | Initial Population | T-30 sec | Log Reduction | % Reduction |
|---|---|---|---|---|
| 1 | 9.10E+07 | 3.00E+01 | 6.48 | 100.0000 |
| 2 | 8.00E+07 | 4.80E+02 | 5.22 | 99.9994 |
| 3 | 6.80E+07 | 1.00E+01 | 6.83 | 100.0000 |
| Average | 7.97E+07 | 1.73E+02 | 6.1788 | 99.9998 |

Example 3

Sterilizing Medical Equipment or any Small Household Items

Figure 7:
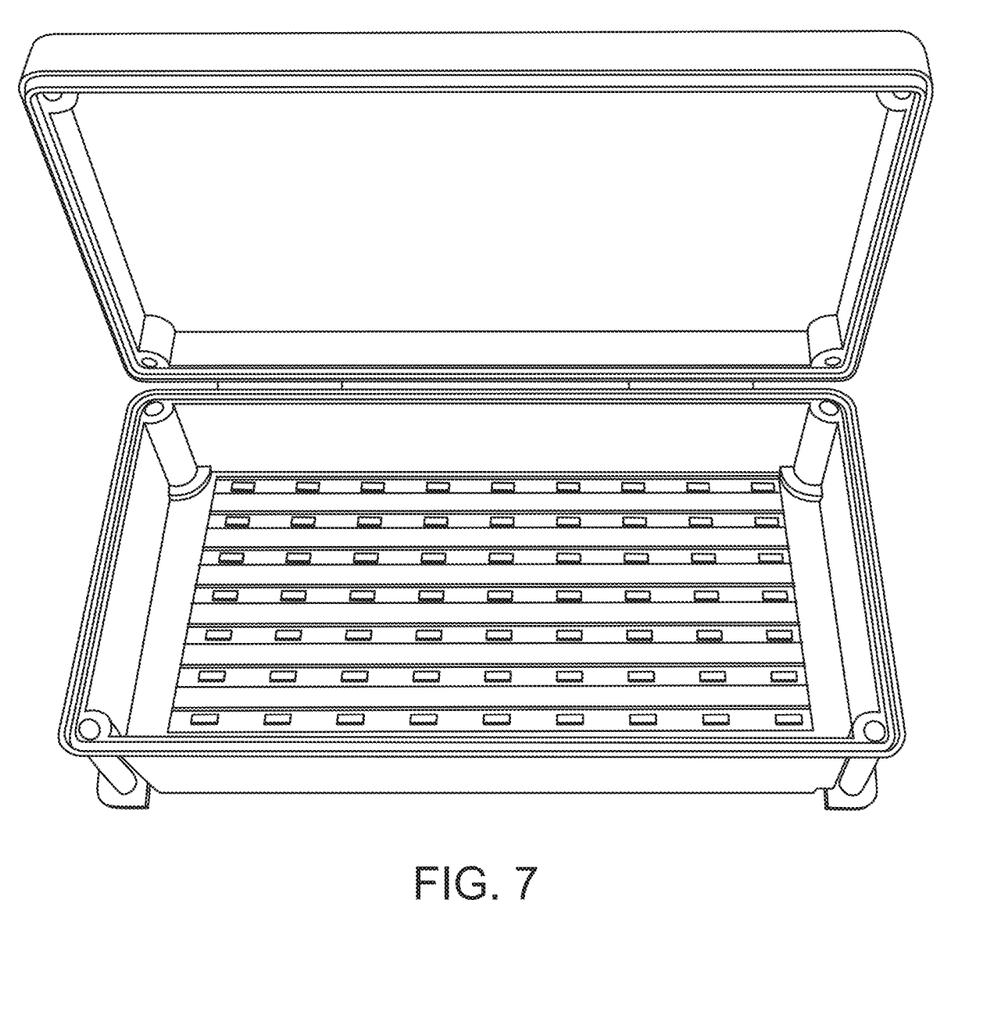
FIG. 7 shows a LED "Purifying Box". LED strips of NIR wavelengths in the range of 850-890 nm, 930-940 nm and violet light of 405 nm are installed inside the device.

According to one preferred embodiment a container is provided for sterilizing medical equipment. FIG. 7 illustrates a prototype of such a container. The container may be a box, such as in FIG. 7 with NIR light strips attached inside the box. The strips may be attached inside the cover of the box or additionally or alternatively inside the bottom and/or the sides of the box. The NIR light strips are preferably as described in Example 1 above.

According to this embodiment the light strips are turned on when the container is closed or the container has a switch to turn the lights on and off. According to one preferred embodiment the lights are automatically turned off after a pre-determined period of time.

According to one preferred embodiment the container serves as a medical tray. The container may include instruments for a specific type of procedure, such as a surgical operation or a dental procedure. The instruments inside the medical tray may be sterilized by autoclaving before inserting them into the container where the light system keeps them sterile until use.

Figure 8:
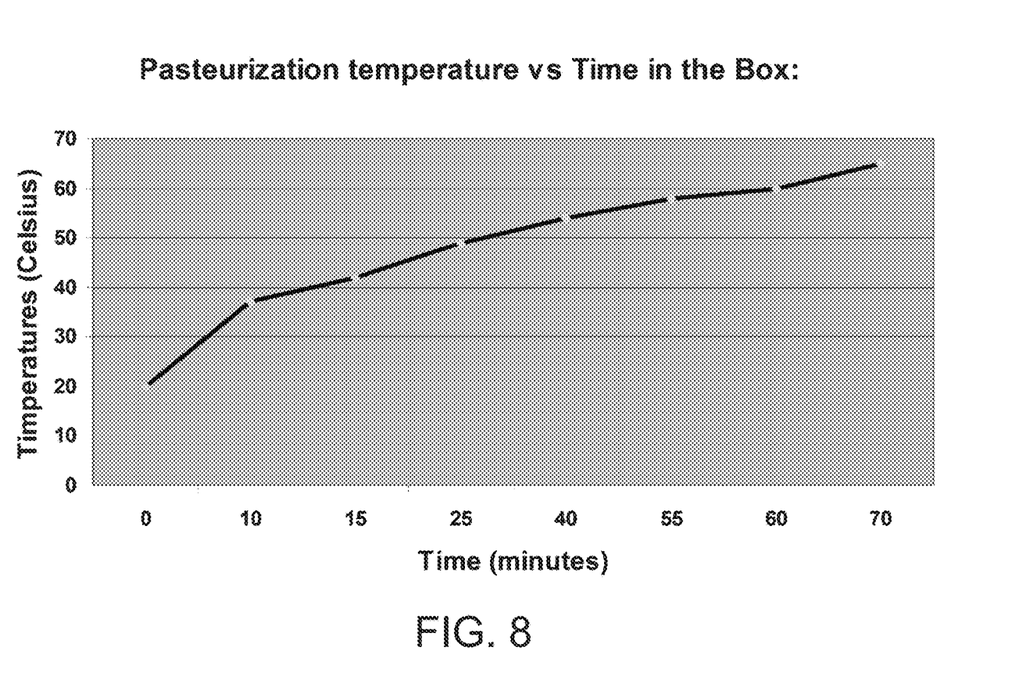
FIG. 8 illustrates the increase of temperature as a function of time of an item closed in the box of FIG. 8.
Figure 9:
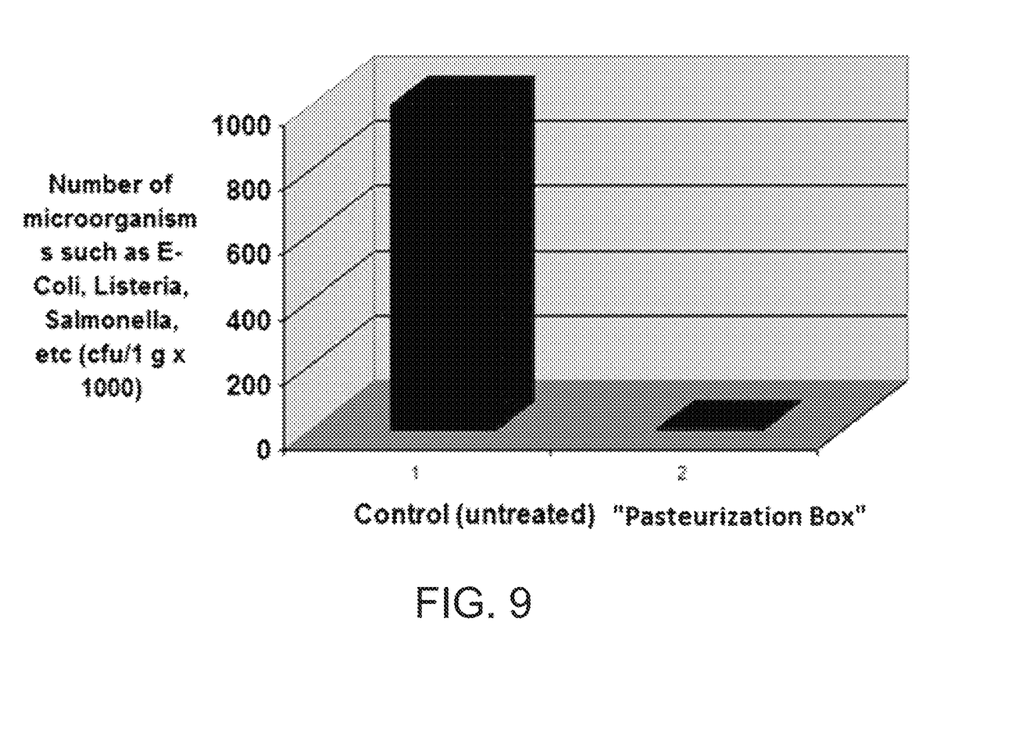
FIG. 9 illustrates the bacterial killing effect of the box of FIG. 7.

FIG. 8 shows how the container may also be used as a purification device. Within 60 minutes the temperature is raised to 63 Celsius degrees which is sufficient for destroying most pathogenic microbes because of the synergistic action between NIR and the temperature rise. FIG. 9 shows the eradication of microbes from items after treating them for 2 hours in the box.

According to one preferred embodiment the container may include an ozone generator that allows ozone to flush through the container.

According to one preferred embodiment the ozone generator has an open air design and will create higher ozone levels than all other 7000 mg/h ozone generators on the market. Heat destroys ozone and placing the 2 plates on top of each other within a small box would create high heat levels that quickly destroy the ozone being created. It will also limit the amount of oxygen from the surrounding air that can access the electrical charge on the plates, thus producing less ozone than the dual transformer unit here.

A container with the lights and an ozone flush may be used also for disinfecting fabric material. Ozone would be particularly effective in such an embodiment because the light may not penetrate to every fold of the fabric.

According to one preferred embodiment the container described above may be used for example at daycare centers to disinfect toys or other children's items. The device for this purpose is specifically designed to diminish norovirus, rotavirus and influenza virus. The device for this purpose is preferably provided with a locking system.

According to one embodiment the container described above may also be used to disinfect any small household or personal items such as watches, jewelry, coins, etc. A skilled artisan would recognize that the device may be used for disinfecting various items and all such uses are within the scope of this invention.

Example 4

Hand or Feet Sanitizing Device

A device to sanitize hands preferably includes one or more cavities to insert hands or feet. The cavities include LED lights or OLED lights providing NIR wavelengths. The wavelengths are preferably selected from the groups consisting of: 800-850 nm, 850-860 nm, 860-880 nm, 880-900 nm, and 930-970 nm. OLED lights may provide wavelengths emitting in the range of 750-820 nm.

Alternatively the device has a flat or curved platform adapting to the hand or feet.

According to one preferred embodiment the device has a sensor that turns the lights on when a person inserts his/her hands or feet in the cavities or on the platform.

According to one embodiment the lights are on for a pre-determined time sufficient to reduce the amount of microbes on hands to a desired level.

According to one embodiment the device also blows hot air to dry hands. According to another embodiment, the device blows ozone to increase the sanitizing effect.

The device may be used in health-care and clinical settings for hand sanitation. It may be installed in places like public bathrooms, schools and daycare centers. Furthermore, the device is practical in swimming facilities, nail salons and gyms for preventing nail and foot fungus infections.

What is claimed is:

1. A method for disinfecting and/or sterilizing a hospital area, said method comprising illumination of the area with light output from:
   one or more LED elements emitting NIR light of a wavelength within a range of 850-890 nm and within a range of 920-960 nm,
   one or more LED elements emitting UV-C light within a range of 240-260 nm, continuously for 5 to 50 minutes, wherein the method reduces microorganisms at least by a reduction level of 5-log, the microorganisms being selected from a group consisting of MRSA, *Staphylococcus aureus*, *Salmonella typhimurium*, and *Clostridium difficile*.

2. The method of claim 1 additionally comprising illumination of the area with light output from one or more of following:
   one or more LED elements emitting light of a wavelength within a range of 380 to 475 nm; and
   one or more LED or OLED elements emitting light of a wavelength within a range of 475 to 700 nm.

3. The method of claim 2, wherein the one or more LED elements emitting UV-C light of a wavelength within a range of 240 to 260 nm are automatically switched off when a detector recognizes an event indicating a human being is present in the area.

4. The method of claim 2, wherein the method additionally includes providing an ozone stream in the area, and wherein the method reduces microorganisms by a reduction level of 7-log within 10 to 20 minutes.

5. The method according to claim 4, wherein the ozone stream is provided by an ozone generator producing at least 1000 mg of ozone per hour.

6. The method of claim 1, wherein the hospital area is a surgery room.

7. The method of claim 1, wherein the microbe is MRSA and the method reduces the microbes by at least 6 log in 30 minutes.

* * * * *